(12) United States Patent
Hofmann et al.

(10) Patent No.: US 7,901,727 B2
(45) Date of Patent: Mar. 8, 2011

(54) REINFORCED POROUS COATING

(75) Inventors: Heinrich Hofmann, Pully (CH); Frederic Neftel, Lausanne (CH); Laurent-Dominique Piveteau, Bussigny (CH)

(73) Assignee: Debiotech S.A., Lausanne (CH)

( * ) Notice: Subject to any disclaimer, the term of this patent is extended or adjusted under 35 U.S.C. 154(b) by 0 days.

(21) Appl. No.: 12/066,114

(22) PCT Filed: Sep. 15, 2006

(86) PCT No.: PCT/IB2006/053327
§ 371 (c)(1),
(2), (4) Date: Jun. 9, 2008

(87) PCT Pub. No.: WO2007/031972
PCT Pub. Date: Mar. 22, 2007

(65) Prior Publication Data
US 2008/0249616 A1 Oct. 9, 2008

(30) Foreign Application Priority Data
Sep. 16, 2005 (EP) .................................. 05108573

(51) Int. Cl.
*B05D 1/00* (2006.01)
*B05D 3/12* (2006.01)
*B05D 1/36* (2006.01)

(52) U.S. Cl. ........ 427/2.1; 427/2.24; 427/2.25; 427/180; 427/202; 427/203; 427/264; 427/271

(58) Field of Classification Search .................... 427/2.1, 427/2.24, 2.25, 180, 202, 203
See application file for complete search history.

(56) References Cited

U.S. PATENT DOCUMENTS
6,709,379 B1 3/2004 Brandau et al.
(Continued)

FOREIGN PATENT DOCUMENTS
WO 98/28025 7/1998
(Continued)

OTHER PUBLICATIONS

Jiang et al. "Large scale fabrication of periodic nanostructured materials by using hexagonal non-closed packed collodial crystals as templates". Langmuir, 2006, vol. 22 (9) pp. 3955-3958.*

(Continued)

*Primary Examiner* — Timothy H Meeks
*Assistant Examiner* — Cachet I Sellman
(74) *Attorney, Agent, or Firm* — Nixon & Vanderhye P.C.

(57) ABSTRACT

The present invention relates to a process for manufacturing a porous coating with structures in the micro or nano-size domain characterized by the following steps: —providing a support having a surface, —depositing on said surface one mono-layer of temporary particles, —depositing a coating on said temporary particles in such a way that the thickness of said coating is less than the particle diameter, —eliminating said temporary particles and thereby obtaining a porous coating, the pores of said coating corresponding to the spaces previously occupied by the temporary particles and at least a part of the pores communicating with the external environment, —applying a coating fixation step, characterized by the fact that said temporary particles are deposited on said surface in such a way that, after particle deposition, more than 50% of the temporary particles are in contact with a maximum of two adjacent particles and otherwise are separated by an empty space. The invention also concerns a coating and an object which can be obtained with this process.

20 Claims, 5 Drawing Sheets

U.S. PATENT DOCUMENTS

2006/0276878 A1\* 12/2006 Owens et al. .............. 623/1.15
2007/0160639 A1 7/2007 Pantelidis et al.

FOREIGN PATENT DOCUMENTS

| WO | 02/43937 | 6/2002 |
|---|---|---|
| WO | 2004/043292 | 5/2004 |
| WO | 2006/063157 | 6/2006 |

OTHER PUBLICATIONS

Cho et al. Two Dimensional, open pored, mesoscopic titania layers using polymeric nanoparticle monolyaers as template. Advanced Materials, 2004, vol. 16 No. 20 pp. 1814-1817.\*

Office Action dated Nov. 24, 2009 from U.S. Appl. No. 11/991,751.

Piveteau et al, "Evaluating mechanical adhesion of sol-gel titanium dioxide coatings containing calcium phosphate for metal implant application," *Biomaterials* vol. 21, No. 21 (Nov. 1, 2000) 2193-2201, XP004216035.

Bartlett et al, "Highly Ordered Macroporous Gold and Platinum Films Formed by Electrochemical Deposition through Templates Assembled from Submicron Diameter Monodisperse Polystyrene Spheres," Chem. Mater. 2002, vol. 14, No. 5, 2199-2208, XP002353386.

Hyodo et al., "Preparation of macroporous SnO2 films using PMMA microspheres and their sensing properties to NOx and H2", *Sensors and Actuators B, Elsevier Sequoia S.A.*, pp. 580-590, XP004867911, Mar. 2, 2005.

Peng Jiang, "Surface-templated nanostructured films with two-dimensional ordered arrays of voids", *Angewandte Chemie*, vol. 43, No. 42, Oct. 2004, pp. 5625-5628, XP002365896.

Park et al., "A facile route to prepare high surface area mesoporous SiC from SiO2 sphere templates", *Journal of Materials Chemistry*, 14(23), pp. 3436-3439, XP002365897, Sep. 22, 2004.

Ko et al., "Fabrication of colloidal self-assembled monolayer (SAM) using monodisperse silica and its use as a lithographic mask", *Preparation and Characterization, Elsevier Sequoia, NL*, vol. 447-448, Jan. 2004, pp. 638-644, XP004493813.

International Search Report for PCT/IB2006/053323 mailed Mar. 7, 2007.

Written Opinion for PCT/IB2006/053323 mailed Mar. 7, 2007.

Hyodo T, et al., "Preparation of macroporous SnO2 films using PMMA microspheres and their sensing properties to N0x and H2", Sensors and Actuators B., pp. 580-590, (May 13, 2005).

Jiang P., "Surface-templated nanostructured films with two-dimensional ordered arrays of voids", Angewandte Chemie. International Ed., vol, 43, No. 42, pp. 5625-5628, (Oct. 25, 2004).

Park, KH et al., "A facile route to prepare high surface area mesoporous SiC from SiO2 sphere templates", Journal of Materials Chemistry, vol, 13, No. 23, pp. 3436-3439, (2004).

Barlett P N et al., "Highly ordered macroporous gold and platinum films formed by electrochemical deposition through templates assembled from submicron diameter monodisperse polystyrene spheres", Chemistry of Materials, vol. 14, No. 5, pp. 2199-2208, (May 20, 2002).

Ko, H Y et al., "Fabrication of colloidal self-assembled monolayer (SAM) using monodisperse silica and its use as a lithographic mask", Preparation and Characterization, vol. 447-448, pp. 638-644, (Jan. 30, 2004).

Piveteau L D et al., "Evaluating mechanical adhesion of sol-gel titanium dioxide coatings containing calcium phosphate for metal implant application", Biomaterials, vol. 21, No. 21, pp. 2193-2201, (Nov. 1, 2000).

International Search Report for International Application No. PCT/IB2006/053327, mailed Jan. 31, 2007.

Written Opinion of the International Searching Authority, mailed Jan. 31, 2007.

Office Action dated Jul. 15, 2010 from U.S. Appl. No. 11/991,751.

Stein et al, "Sphere templating methods for periodic porous solids," Microporous and Mesoporous Materials, 44-45 (2001) 227-239.

Bartlett et al, "Highly Ordered Macroporous Gold and Platinum Films Formed by Electrochemical Deposition through Templates Assembled from Submicron Diameter Monodisperse Polystyrene Spheres," Chem. Mater. 14 (2002) 2199-2208.

Office Action dated Sep. 27, 2010 from U.S. Appl. No. 11/991,751.

Bartlett et al, "Highly Ordered Macroporous Gold and Platinum Films Formed by Electrochemical Deposition through Templates Assembled from Submicron Diameter Monodisperse Polystyrene Spheres," Chem. Mater. 2002, 14, 2199-2208.

Stein et al, "Sphere templating methods for periodic porous solids," Microporous and Mesoporous Materials, 44-45 (2001) 227-239.

\* cited by examiner

REINFORCED POROUS COATING

This application is the U.S. national phase of International Application No. PCT/IB2006/053327, filed 15 Sep. 2006, which designated the U.S. and claims priority to EP 05108573.6, filed 16 Sep. 2005, the entire contents of each of which are hereby incorporated by reference.

FIELD OF INVENTION

The present invention relates to porous coatings with controlled structure in the micro and nano-size domain. In particular, but not exclusively, it relates to processes for fabricating such surfaces and to objects obtained according to such processes.

BACKGROUND OF THE INVENTION

Various techniques have been employed to achieve the preparation of porous coatings using colloidal particles. They can be classified in laser techniques [Hua1, Li1], classical colloidal, or nanosphere, lithography [Ko1, Jia3, Den2, Ryb1], soft lithography [Cho2], three-dimension particle template deposition and infiltration techniques [Jia1, Par, Sch, Hyo1, Bar] or one-step deposition techniques [Kan1, Xu1]. The references between square brackets are copied below:

[Jia1] P. Jiang, "Surface-templated nanostructured films with two-dimensional ordered arrays of voids", Ange. Chem. Int. Ed. 2004, 43, 5625-5628.

[Hua] S. M. Huang, M. H. Hong, B. S. Luk'yanchuk, Y. W. Zheng, W. D. Song, Y. F. Lu, T. C. Chong, "Pulsed laser-assisted surface structuring with optical near-field ehanced effects", J. Appl. Phys. 2002, 92(5), 2495-2500.

[Ko] H.-Y. Ko, H.-W. Lee, J. Moon, "Fabrication of colloidal self-assembled monolayers (SAM) using monodisperse silica and its use as a lithographic mask", Thin Solid Films 2004, 447-448, 638-644.

[Sch] R. C. Schroden, M. Al-Daous, C. F. Blanford, A. Stein, "Optical properties of inverse opal photonic crystals", Chem. Mater. 2002, 12, 3305-3315.

[Jia2] P. Jiang, M. J. McFarland, "Wafer-scale periodic nanohole arrays templated from two-dimensional nonclose-packed colloidal crystals", J. Am. Chem. Soc. 2004, 127, 3710-3711.

[Kan] M. Kanungo, M. M. Collinson, "Fabrication of two-dimensionally ordered macroporous silica materials with controllable dimensions", Chem. Comm. 2004, 548-549.

[Li] L. P. Li, Y. F. Lu, D. W. Doerr, D. R. Alexander, J. Shi, J. C. Li, "Fabrication of hemispherical cavity arrays on silicon substrates using laser-assisted nanoimprinting of self-assembled particles", Nanotechnology 2004, 15, 333-336.

[Par] K.-H. Park, I.-K. Sung, D.-P. Kim, "A facile route to prepare high surface area mesoporous SiC from $SiO_2$ sphere templates", J. Mater. Chem. 2004, 14 3436-3439.

[Bri] E. P. Briggs, A. R. Walpole, P. R. Wilshaw, M. Karlsson, E Palsgard, "Formation of highly adherent nano-porous alumina on Ti-based substrates: a novel bone implant coating", J. Mater. Sci.: Mat. Med. 2004, 15, 1021-2029.

[Den] F. A. Denis, P. Hanarp, D. S. Sutherland, Y. F. Dufrêne, "Nanoscale chemical patterns fabricated by using colloidal lithography and self-assembled monolayers", Langmuir 2004, 20, 9335-9339.

[Cho] D.-G. Choi, S. G. Jang, H. K. Yu, S.-M. Yang, "Two-dimensional polymer nanopattern by using particle-assisted soft lithography", Chem. Mater. 2004, 16, 3410-3413.

[Ryb] J. Rybczynski, U. Ebels, M. Giersig, "Large-scale, 2D arrays of magnetic nanoparticles", Col. Surf. A: Physicochem. Eng. Aspects, 2003, 219, 1-6.

[Xu] H. Xu, W. A. Goedel, "Polymer-silica hybrid monolayers as precursors for ultrathin free-standing porous membranes", Langmuir 2002, 18(6), 2363-2367.

[Hyo1]T. Hyodo, K. Sasahara, Y. Shimizu, M. Egashira, "Preparation of macroporous $SnO_2$ films using PMMA microspheres and their sensing properties to NOx and H2", Sens. Act. B 2005, 106, 580-590.

[Bar] P. N. Bartlett, J. J. Baumberg, P. R. Birkin, M. A. Ghanem, M. C. Netti, "Highly ordered macroporous gold and platinum films formed by electrochemical deposition through templates assembled from submicron diameter monodisperse polystyrene spheres", Chem. Mater. 2002, 14, 2199-2208.

GENERAL DESCRIPTION OF THE INVENTION

The present invention offers another approach for fabricating porous coatings in the micro or nano-size domain.

To this effect it relates to a process for manufacturing a porous coating with structures in the micro or nano-size domain characterized by the following steps:
  providing a support having a surface,
  depositing on said surface one mono-layer of temporary particles,
  depositing a coating on said temporary particles in
  such a way that the thickness of said coating is less than the particle
  diameter,
  eliminating said temporary particles and thereby obtaining a porous
  coating, the pores of said coating corresponding to the spaces previously occupied by the temporary particles and at least a part of the pores communicating with the external environment,
  applying a coating fixation step,
characterized by the fact that said temporary particles are deposited on said surface in such a way that, after particle deposition, more than 50% of the temporary particles are in contact with a maximum of two adjacent particles and otherwise are separated by an empty space.

In the process, the temporary particles and the coating may be deposited together as a slurry.

Preferred processes according to the invention are defined in the dependent claims.

The invention also relates to a porous coating with structures in the micro or nano-size domain obtained according to a process as defined in anyone of the previous claims, said porous coating having more than 50% of the pores which are not in contact and separated by an empty space.

Preferred porous coatings according to the invention are defined in the dependent claims.

Finally, the invention relates also an object comprising a coating as defined above.

Preferred objects according to the invention are defined in the dependent claims.

Using the present invention allows a precise control of the porosity, the chemical composition and the thickness of the coating. It also offers the advantage of producing coatings with relatively important porosities and thickness. By maintaining a certain distance between the pores, it allows the production of mechanically more strong coatings. Cavities with sizes between several tenths of nanometers and a few tenths of microns and porosities of 60% can be achieved. Thickness greater than 200 nm can be obtained allowing thereby the manufacturing of specific objects with the capacity to store a significant amount of a given substance or with a significant porosity to allow tissue ingrowth. These can be used for various applications such as, but not exclusively, drug eluting stents, porous or drug eluting orthopedic implants, porous or drug eluting dental implants.

In the present text, the term "eliminating" is used in a broad sense. It covers any commonly used terms related to an important change in the particle morphology, such as for example disintegration, dissolution or removal. For instance, but not exclusively, elimination of the temporary particles may comprise a thermal step, a chemical step, a mechanical step, an electromechanical or an irradiation step. In the case of a thermal, a chemical or an irradiation step, the temporary particles are either completely destroyed or only partially, e.g. the particles can be made hollow. In the case of a mechanical step, the temporary particles can be mechanically removed. In the case of an electromechanical step (e.g. sonication or ultrasonic vibrations), the particles can be swelling (e.g. by use of polymeric particles, such as PLGA) or disintegrated.

The term "temporary" has to be understood as "present only for a limited time during the process". Temporary particles can be viewed as templates that create the tri-dimensional structure and porosity of the coating.

The expression "mono-layer of particles" means that the particles are at the same level relatively to the surface of the support. For each mono-layer, no particle will sit on top of another.

Substrate

The substrate can be made of any type of material: metal, ceramic or polymer. Metals such as stainless steel, Nitinol, titanium, titanium alloys, or aluminum and ceramics such as zirconia, alumina, or calcium phosphate are of particular interest. Furthermore, the substrate can also be made of a layer of temporary particles.

Coating Composition

In the same way, the coating can be made of different types of materials: metals, ceramics, polymers, hydrogels or a combination of any of these materials. For example, the coating can be made of a ceramic with an organic binder. Such combination reduces the risk of crack formation at the surface.

As the porous coating may be in contact with a living body, it is preferably made of a biocompatible material. Depending on applications this can be, but not exclusively, an oxide, a phosphate, a nitride or a carbonitride. Among the oxide the following ones are preferred: tantalum oxide, aluminum oxide, zirconium oxide or titanium oxide. When using aluminum, the process may advantageously comprise a further anodisation step, which both increases the biocompatibility and further creates a nanoporous additional structure.

Particles

The diameter and the shape of the temporary particles can be chosen arbitrarily. But a preference is given for homogeneous particles in shape and size. The chemical composition of the particles is also free, but it is preferably selected in the group of polymers, starch, silica, metals or biological materials such as cells. A preference is given for polymers materials with a spherical shape and homogeneous diameter: mono-disperse polymer beads. For example, polystyrene bead may be advantageously used. They are readily available in numerous sizes and are very consistent in size. Alternatively, biocompatible polymers (e.g. PLGA or Poly Lactide Glycolide Acid type) can also be used.

When deposited on the support and before the coating deposition, more than 50% of the temporary particles are in contact with a maximum of two particles and otherwise are separated by an empty space. Such a configuration decreases the pore density, creates continuous walls between the pores and therefore mechanically reinforces the coating.

An aggregate of particles is a group or a subgroup of closely packed particles wherein at least one particle is in direct contact with three other particles. When deposited on a surface, temporary particles have a tendency to form small aggregates due to capillary forces acting between them.

In order to avoid aggregation of particles and maintain a certain distance between them, several methods can be envisaged. Hereafter a non-limiting list of potential approaches is given.

In a first embodiment, the particles are charged and therefore repulsion occurs between particles maintaining a certain distance between them.

In another embodiment particles are coated with long polymeric chains extending towards the outside. Steric repulsion provoked by these chains will maintain a certain distance between the particles.

In another embodiment, a layer of ceramic nanoparticles mixed to a dispersing agent is first deposited onto the substrate. The presence of this layer limits the movements of the particles when they are then deposited onto the substrate and therefore counteract the capillary forces.

In another embodiment, a soft layer is first deposited onto the substrate. When particles are deposited onto this layer, they slightly penetrate the layer and therefore cannot move freely anymore.

Using hydrophilic and/or hydrophobic temporary particles allows the creation of various structures in the coating. Before the deposition of the temporary particles, the substrate is locally covered with a hydrophilic respectively a hydrophobic layer. In this way specific zones are adapted to fix temporary particles with a similar surface affinity while attachment on the other zones is prevented. In the case of a stent, it may be advantageous to only coat regions which are less subject to deformations; alternatively it may be advantageous to only coat regions which are in contact with the intima of the vessel to target the release of drug to prevent proliferation or inflammation. In the case of bone or dental implants, it may be advantageous to select regions where bone ingrowth should be favored and where it should be hindered.

Coating Deposition

Different procedures can be considered for the coating deposition. They are chosen according to the coating precursors that are used as well as to the desired properties of the coating. A few examples are given below:

A first procedure to deposit the coating onto the substrate uses a mixture of nanoparticles in a solvent such as for example water as coating precursor. The substrate is dipped into the precursor mixture and pulled out at a controlled speed.

The thickness of the coating varies with the viscosity of the mixture and with the pulling speed.

Another procedure uses a sol obtained through hydroxylation and partial condensation of a metallic alkoxyde as coating precursor. Again, the precursor can be coated onto the substrate using either dip or spin coating.

In an other procedure, a slurry containing both the removable particles and the coating precursor dissolved in, for example, water is coated onto the substrate.

In all cases the coating can be deposited in several steps or sublayers. Between the depositions of each sub-layer the solvent of the coating precursor can be partially or fully removed by, for example, a thermal treatment. This approach permits the formation of thicker, crack-free coatings. The composition of the coating precursor can also be modified between each step. This allows the creation of coatings with variable chemical composition. For example, the chemical composition of the coating can be very similar to that of the substrate at the coating/substrate interface and can be very compatible at the interface with the body.

Using nanopowders or a sol-gel approach for producing coatings offers the advantage of reducing the necessary temperature for obtaining crystalline coatings. This is particularly favorable for metallic substrates that may go through phase transitions when thermally treated and therefore lose part of their mechanical or shape memory properties.

An example of such process would be the use of Zircon nanopowder (obtained from Buhler, Uzwil, Switzerland), which enables a sintering between 1,100° C. and 1,200° C. instead of between 1,400° C. and 1,500° C. for standard Zircon powder.

Similar results are obtained with titanium sols produced from tetrabutyl ortho-titanate hydrolized with a mixture of water and nitric acid in absolute ethanol. Crystalline TiO2 in an anatase phase is obtained after a thermal treatment of a few minutes in air between 600° C. and 850° C.

Particles Removal

The elimination of the temporary particles can be achieved by different methods such as for example, but not exclusively, a thermal, a chemical, a mechanical, an electro-mechanical, a photo-chemical or an irradiation step. It can also take place at different stages of the process, before and/or during and/or after the fixation step, depending on the coating requirements Fixation Any appropriate method can be used for the fixation step. Advantageously a drying step is used.

For ceramics this can be sintering where the crystalline phase is formed. For a polymer this can be a photo-chemically (by visible of UV light), a thermally or chemically induced polymerisation. For metals or for certain ceramics this can be a thermal treatment under controlled (neutral or reducing) atmosphere.

Filling of the Coating

Once created, the pores may be filled with a drug of interest, e.g. by dip-coating. The pH of the solution containing the drug can be also adjusted to change the charge present at the surface of the coating and thus facilitating the penetration of the drug into the pores. Another way to facilitate loading is to make pores out of a hydrophobic respectively hydrophilic materials and fill them with a lipophilic respectively hydrophilic solution.

Loading the implant with different drugs can be achieved by creating cavities of different sizes. The cavities are then filled with drug loading vesicles of different sizes, whereby the larger cavities are filled first with larger vesicles (i.e. large vesicles are too big to fill the smaller cavities) and smaller cavities are later filled with smaller vesicles which will fill the remaining places available (i.e. in the small cavities remaining empty). Such a technique enables to store different drugs into the coating which may have different delivery profiles in time which may depend e.g. on the release properties of the vesicles selected (such as hydrophobic or hydrophilic properties; or polymer degradation properties).

Furthermore, the cavities (pores) may be filled by any other appropriate liquid or solid substance, e.g. growth factors, bone cells, other cells, etc. . . . .

Double D & d Coating

A special type of coating covered by this invention is made by depositing two types of temporary particles of different diameters D and d. The process is similar to that presented above and is characterized by the fact that the support is made of temporary particles.

Advantageously more than 50% of the temporary particles which constitute said support are in contact with a maximum of two adjacent particles and otherwise are separated by an empty space.

In a preferred embodiment, the temporary particles which constitute said support have a larger diameter than the particles deposited on said support.

In this process, the cavities (or porosity) obtained in place of the particles of D size will be in open contact with the cavities (or porosity) obtained in place of particles of d size at the former contact points between D particles and d particles, thereby limiting the size of the exit of the D cavities, through the former d particles layer, to a limited size which is defined by either the size of the openings obtained at the contact points between the former D particles and d particles or to the maximum pore size obtained at the outside of the former d particles layer.

By changing the wettability of the particles, the size of the contact points of the pores can be modified. It can be decreased by using hydrophilic particles and increased by using hydrophobic ones.

This technique is particularly interesting for enabling an important drug loading into the large cavities produced by the large particles, while limiting the release in time of such drug though smaller pores resulting from the former smaller particles.

Object

The processes previously discussed allow the manufacturing of objects with specific and original features. These objects structurally differ from the prior art objects due to the specific processes used.

A major application for these objects is in the field of medical implants. Of particular interest are stents, orthopedic and dental implants. The porosity can be used as a drug reservoir that will release its content in a controlled way over time or it can be used to favor tissue ingrowth and therefore increase the mechanical interlocking between the implant and the living tissue.

For stents the coating can be loaded with one or several drugs. It can be a combination of the following drugs given as non-exclusive examples: an anti-proliferative agent, an anti-coagulation substance, an anti-infectious, an bacteriostatic substance.

The object can also be an orthopedic or dental implant wherein the pores may be adapted in the same manner as for the stent discussed above. In such case, the porosity obtained can either be of interest to store growth factors such as bone growth factors, increase biocompatibility or create regions where bone or cartilaginous tissue can grow and attach in a solid manner to the implant. This can also be achieved by filling the cavities with resorbable bioactive ceramics such as calcium phosphates.

The pore size may also be adapted for diffusing beads, particles or polymers containing an active substance which can be slowly released.

Alternatively the beads or particles can emit an irradiation. Advantageously, in such case, the beads or particles shall remind within the cavities.

FIGURES AND TABLES

The present invention will be more fully understood from the following figures and table:

TABLE 1

Figure 1:
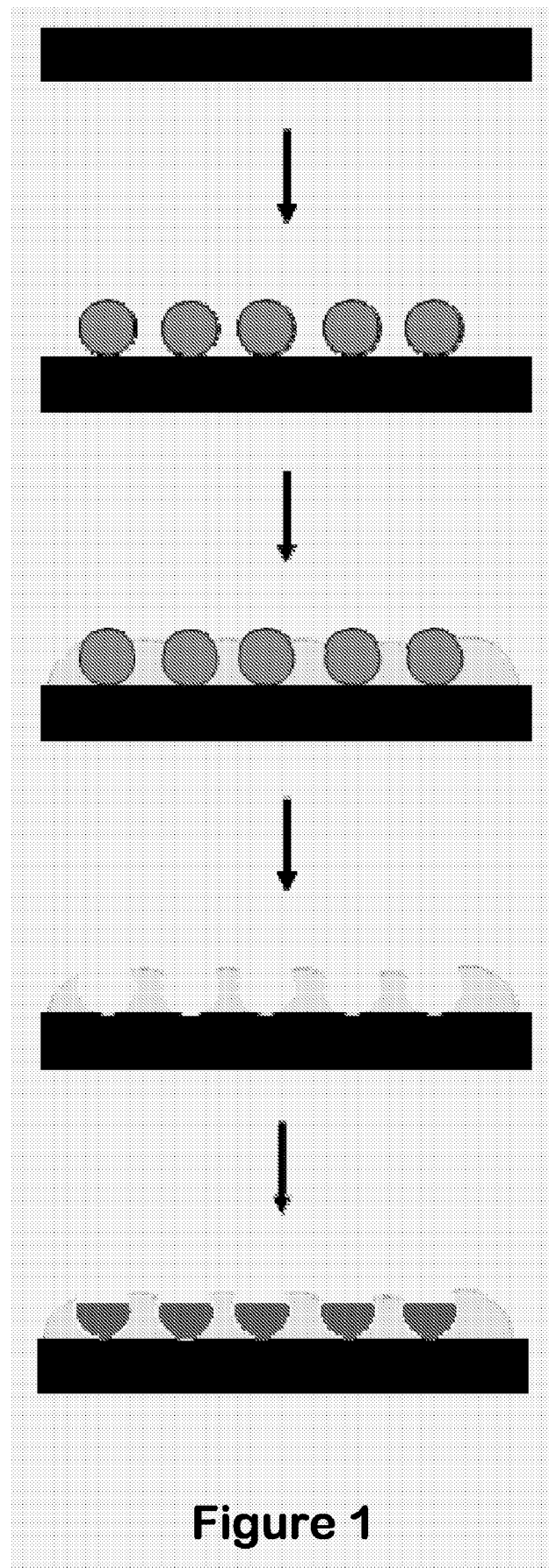
FIG. 1 is a schematic representation of a process according to the invention for manufacturing a coating with one layer of pores.
Figure 2:
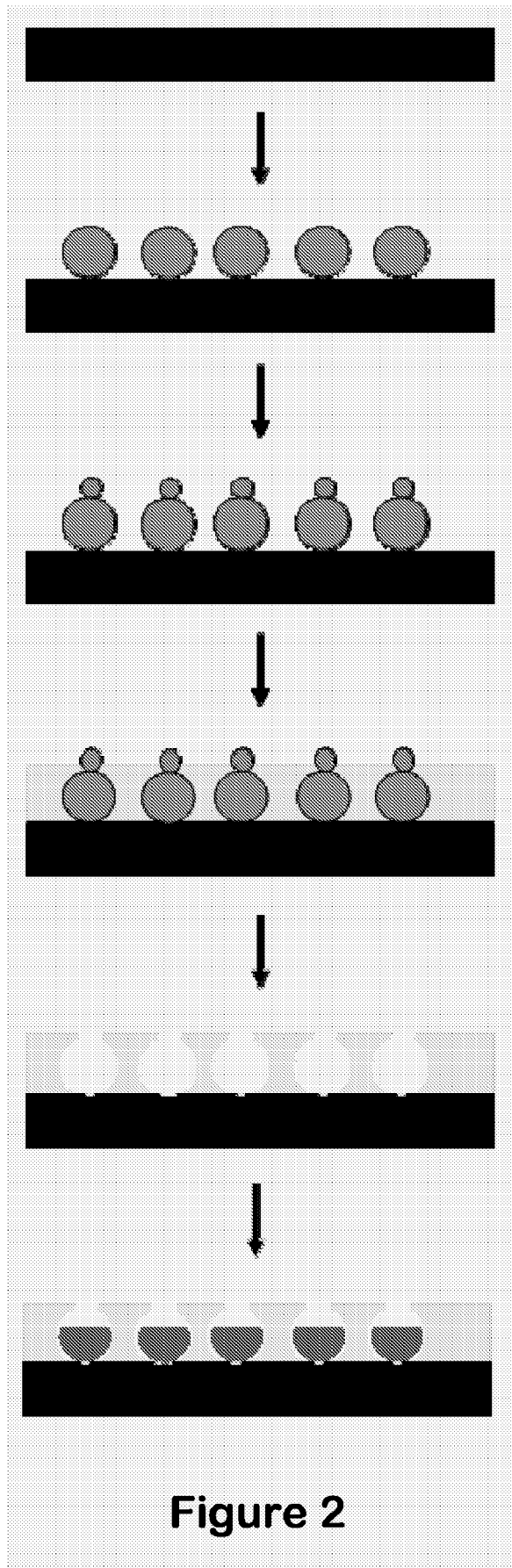
FIG. 2 is a schematic representation of a process according to the invention for manufacturing a coating with two layers of pores.
Figure 3:
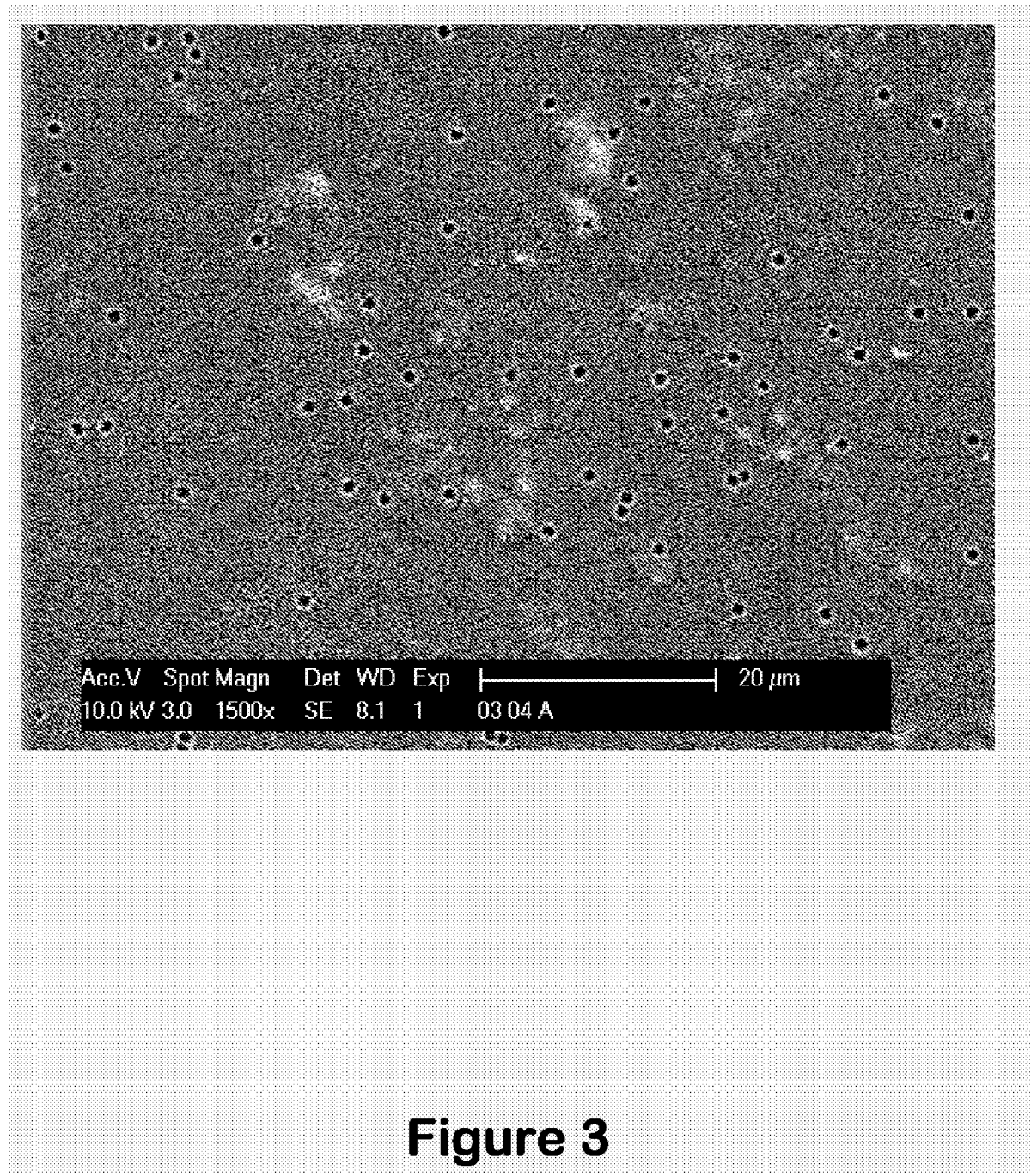
FIG. 3 shows a picture of an embodiment of the invention. It is described at the first example in this patent.
Figure 4:
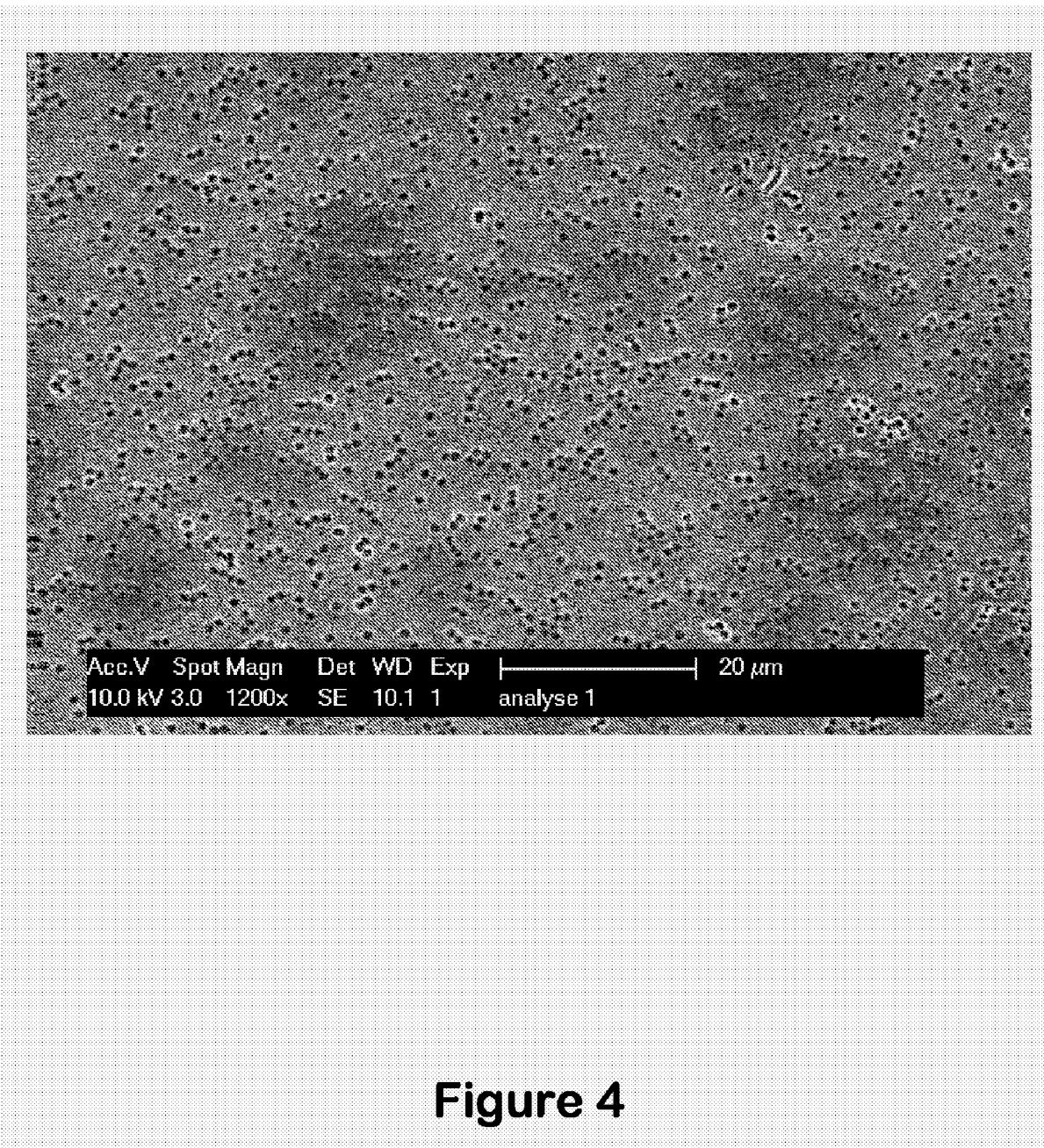
FIG. 4 shows an example of a porous surface according to the invention. It is described in the second example.
Figure 5:
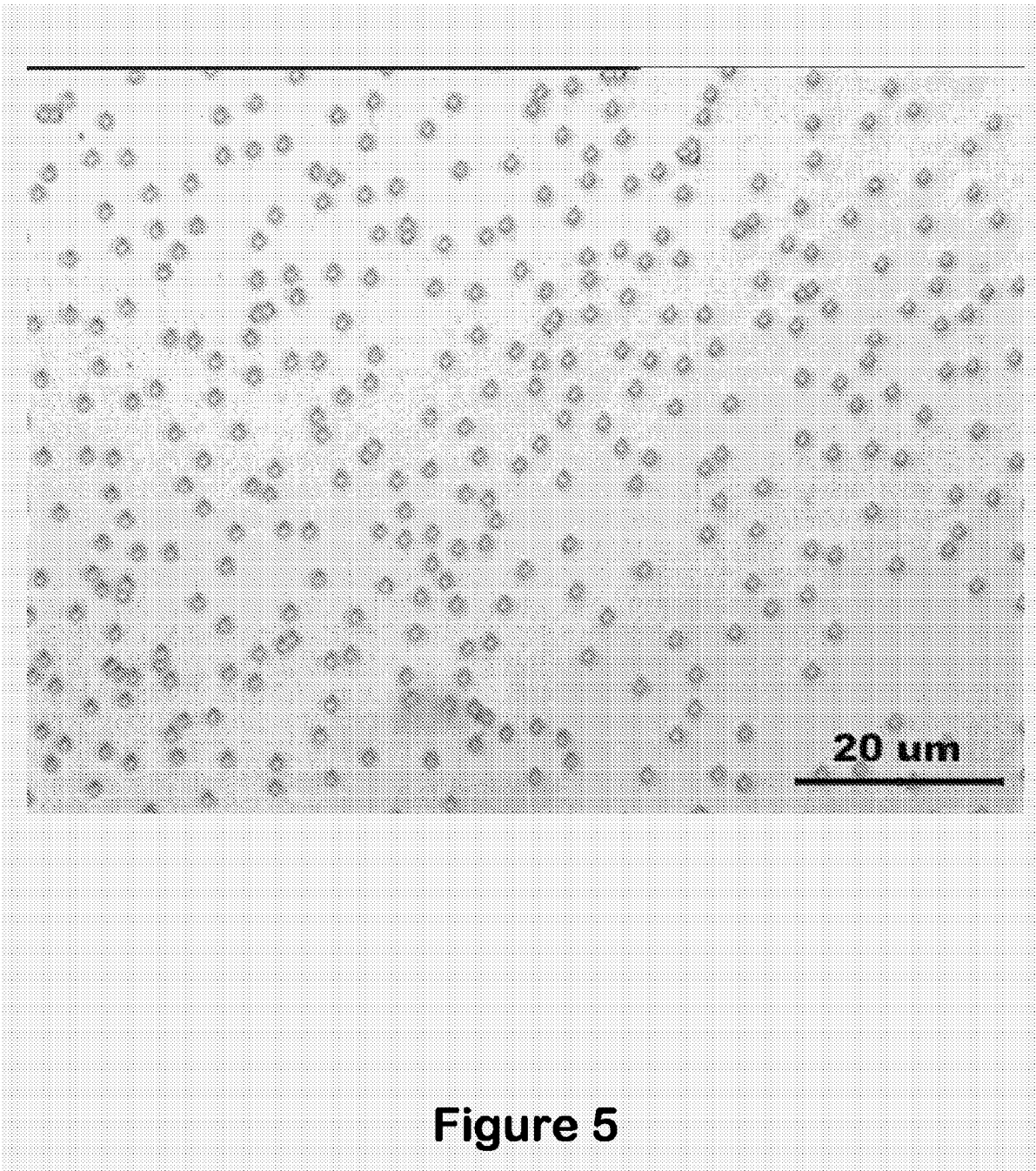
FIG. 5 shows an example of dispersed temporary particles on a substrate before the deposition of the coating Table 1 below summarizes different possibilities for manufacturing a porous surface according to the present invention

| Colloidal mask's materials | Coating's material | Consolidation techniques | Elimination methods of the colloids: before, during or after the consolidation step |
| --- | --- | --- | --- |
| Polymer | Polymer | UV-, Thermal-Polymerisation | After-Chemical selective dissolution |
| Polymer | Metal | Thermal-Annealing, . . . | Before or after-Chemical selective dissolution Before or after-UV-irradiation, oxygen plasma During-Pyrolsis After-Mechanical (ultrasonic, . . . ) |
| Polymer | Ceramics | Thermal-Sintering | Before Chemical selective dissolution Before-UV-irradiation, oxygen plasma During-Pyrolysis |
| Metal | Polymer | UV-, Thermal-Polymerisation | After-Chemical selective dissolution |
| Metal | Ceramics | Thermal-Sintering | Before-Chemical selective dissolution |
| Ceramics | Polymer | UV-, Thermal-Polymerisation | After-Chemical selective dissolution After-Mechanical (ultrasonic, . . . ) |
| Ceramics | Metal | Thermal-Annealing, . . . | Before or after-chemical selective dissolution After-Mechanical (ultrasonic, . . . ) |
| Ceramics | Ceramics | Thermal-Sintering | Before or after-chemical selective dissolution |

ILLUSTRATIVE EMBODIMENTS

Example 1

FIG. 3

A layer of titanium dioxide is deposited onto a substrate of stainless steel 316L by dip coating. A pull-out speed of 90 mm/min is chosen. The composition of the titanium dioxide precursor suspension is the following:
  50% of a concentrated suspension of titanium dioxide particles. This suspension is obtained for TechPowder SA, Ecublens, Switzerland. Nanoparticle size is 20 nm and mean aggregation size is 47 nm.
  50% of a poly vinyl alcohol solution diluted to 7%.
  Technical ammonia is used to adjust the pH of the suspension to 10. pH is controlled using a pH-meter.
  This layer is dried during 10 minutes in ambient air.

Then the sample covered with the layer of titanium dioxide is dipped into a suspension of polystyrene (PS) beads of 1 mm diameter. Concentration of this solution in polystyrene beads is 1% wt. It is obtained by diluting a 10% wt solution obtained from Duke Scientific, Fremont, Calif., USA.

The sample is dried in free air. Surface concentration of particles is 12,000 beads/mm$^2$.

Finally the sample is coated with the same titanium precursor as above with the same pull-out speed. After this coating step, sintering takes place as follows: from 20° C. to 500° C. at 1° C./min for the debonding step, then up to 1,400° C. at 10° C./min and finally, from 1,400° C. to 20° C. at 7° C./min.

Example 2

FIG. 4

A titanium dioxide layer is deposited onto a stainless steel substrate as in example 1. After drying this layer, the coated substrate is dipped into a dispersion of PS beads with a 5% wt concentration of PS. The sample is dried in free air and the second ceramic layer is coated as described above. Surface concentration of particles is 120,000 beads/mm$^2$.

The invention claimed is:

1. Process for manufacturing a porous coating with structures of micro or nano-size domain comprising the following steps:
  providing a support having a surface,
  depositing on said surface one mono-layer of temporary particles,
  depositing a coating on said temporary particles in such a way that the thickness of said coating is less than the particle diameter,
  eliminating said temporary particles and thereby obtaining a porous coating having pores, the pores of said coating corresponding to the spaces previously occupied by the temporary particles and at least a part of the pores communicating with the external environment,
  applying a coating fixation step,
  wherein said temporary particles are deposited on said surface in such a way that, after particle deposition, more than 50% of the temporary particles are in contact with a maximum of two adjacent particles and otherwise are separated from other particles by an empty space, and
  wherein the process has no etching step after the depositing step.

2. Process according to claim 1 wherein, after particle deposition more than 70% of the temporary particles are in contact with a maximum of two adjacent particles and otherwise are separated from other particles by an empty space.

3. Process according to claim 1 wherein said temporary particles are charged and therefore repulsion occurs between particles maintaining a certain distance between them.

4. Process according to claim 1 wherein said temporary particles are coated with long polymeric chains extending towards the outside in such a way that steric repulsion provoked by these chains maintains a certain distance between the particles.

5. Process according to claim 1 wherein a layer of ceramic nanoparticles mixed with a dispersing agent is first deposited onto the substrate so that the presence of this layer limits the movements of the particles when they are then deposited onto the substrate and therefore counteract the capillary forces.

6. Process according to claim 1 wherein a soft layer is first deposited onto the substrate so that when particles are deposited onto this layer, they slightly penetrate the layer and therefore cannot move freely anymore.

7. Process according to claim 1 further comprising a filling step where said pores are at least partially filled with a liquid or solid substance.

8. Process according to claim 7 furthermore comprising a covering step wherein the porous coating is covered with a biodegradable substance that will dissolve over time.

9. Process according to claim 8 wherein the biodegradable substance contains a substance to be released for medical purpose.

10. Process according to claim 1 wherein said temporary particles have at least two different diameters.

11. Process according to claim 1 wherein said support is made of temporary particles.

12. Process according to claim 11 wherein more than 50% of the temporary particles which constitute said support are in contact with a maximum of two adjacent particles and otherwise are separated by an empty space.

13. Process according to claim 11 wherein the temporary particles which constitute said support have a larger diameter than the particles deposited on said support.

14. Process according to claim 13 wherein the pores formed on said support are at least partially filled with a liquid or solid substance.

15. Process according to claim 1 wherein the temporary particles and the coating are deposited together as a slurry.

16. Process according to claim 1 wherein the substrate is first partially or fully covered by a hydrophobic respectively hydrophilic layer creating hydrophobic respectively hydrophilic domains on the substrate.

17. Process according to claim 1 wherein hydrophobic respectively hydrophilic particles are used to build the monolayer of temporary particles exclusively onto hydrophobic respectively hydrophilic domains of the substrate.

18. Process according to claim 1 wherein the coating fixation step takes place before the particle elimination step.

19. Process according to claim 1 wherein the coating fixation step takes place simultaneously with the particle elimination step.

20. Process according to claim 1 wherein the coating fixation step takes place after the particle elimination step.

* * * * *